United States Patent [19]

Vora

[11] 4,275,255
[45] Jun. 23, 1981

[54] CONVERSION OF MIXED BUTANES INTO GASOLINE

[75] Inventor: Bipin V. Vora, Elk Grove Village, Ill.

[73] Assignee: UOP Inc., Des Plaines, Ill.

[21] Appl. No.: 112,484

[22] Filed: Jan. 16, 1980

[51] Int. Cl.³ .............................................. C07C 2/58
[52] U.S. Cl. .................................. 585/315; 585/314; 585/331; 585/332; 585/723
[58] Field of Search ............... 585/314, 315, 331, 332, 585/723

[56] References Cited

U.S. PATENT DOCUMENTS

| | | | |
|---|---|---|---|
| 2,314,435 | 3/1943 | Allender | 585/315 |
| 3,172,834 | 3/1965 | Kozlowski | 585/331 |
| 3,233,007 | 2/1965 | Chapman | 585/314 |
| 3,409,540 | 11/1968 | Gould et al. | 585/324 |
| 3,650,743 | 3/1972 | Schuller | 585/332 |
| 3,704,334 | 11/1972 | Dixon et al. | 585/314 |
| 3,800,003 | 3/1974 | Sobel | 585/332 |
| 3,904,384 | 9/1975 | Kemp et al. | 44/56 |
| 3,931,352 | 1/1976 | Mikulicz | 585/737 |
| 4,167,531 | 9/1979 | Potts | 585/723 |

Primary Examiner—Curtis R. Davis
Attorney, Agent, or Firm—James R. Hoatson, Jr.; John F. Spears, Jr.; William H. Page, II

[57] ABSTRACT

A hydrocarbon conversion process for the production of motor fuel blending stocks from butanes is disclosed. The butane feed stream enters a deisobutanizer column. A normal butane-rich stream removed from the deisobutanizer is passed into an isomerization zone, with isomerization zone effluent being returned to the deisobutanizer. An isobutane-rich deisobutanizer overhead stream is passed through a dehydrogenation zone which contains a depropanizer and then into an alkylation zone. The effluent of the alkylation zone is fractionated into a product stream and recycle streams passed into the deisobutanizer and the depropanizer. The utilities cost of operating the process is lowered by integration of the heat exchange required in the process.

8 Claims, 1 Drawing Figure

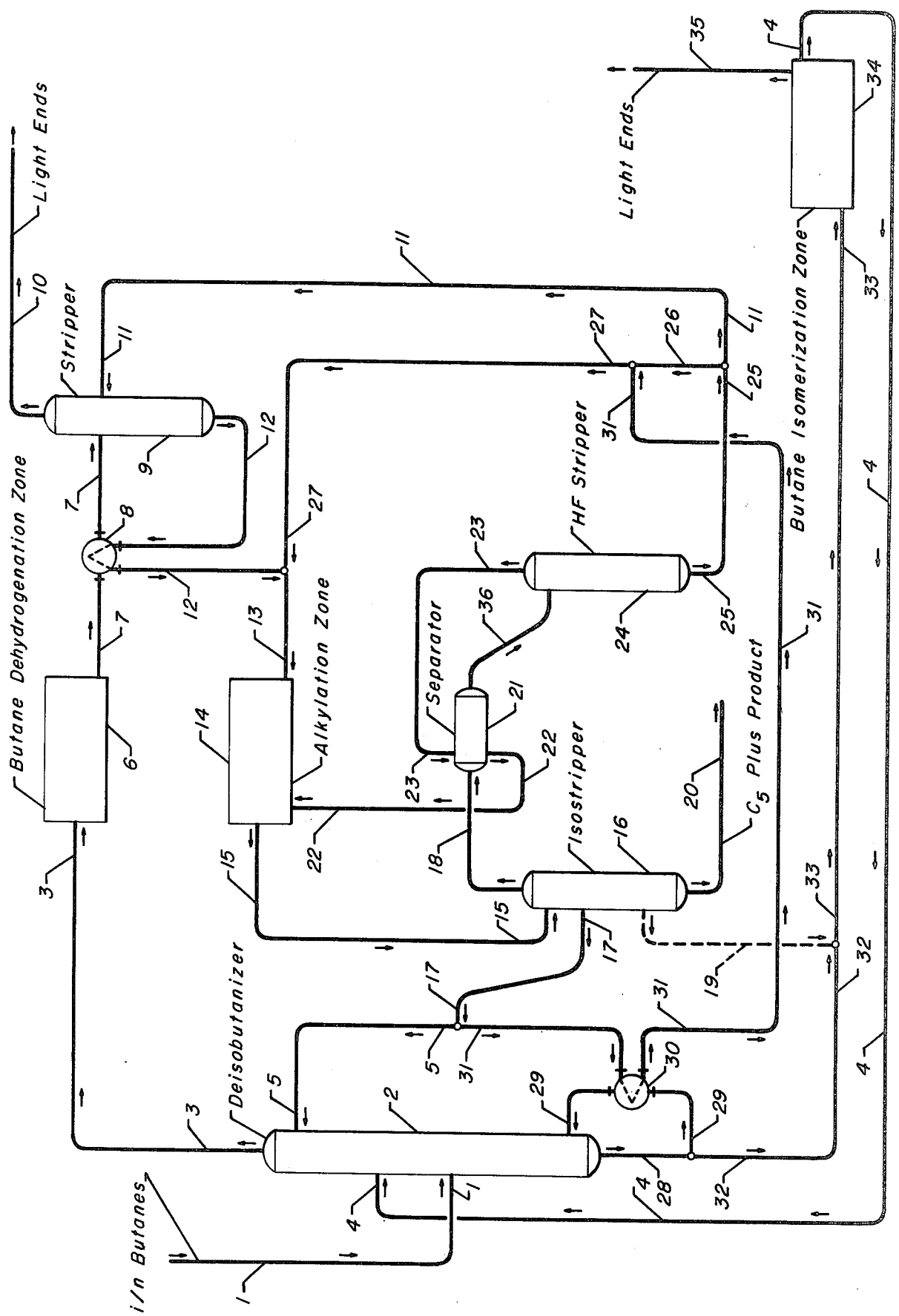

CONVERSION OF MIXED BUTANES INTO GASOLINE

FIELD OF THE INVENTION

The invention is a multi-step hydrocarbon conversion process which comprises the isomerization of butanes, the dehydrogenation of butanes and the alkylation of $C_4$ hydrocarbons. Processes of this nature are often classified in Classes 585 and 208. The invention is directly related to a process for the production of a $C_8$ gasoline blending stock from saturate $C_4$ hydrocarbons.

PRIOR ART

The production of motor fuel by the alkylation of light paraffins with $C_3$ and/or $C_4$ olefins is a widely practiced commercial process. Liquids phase hydrofluoric acid (HF) is often employed as the catalyst. This process is described in U.S. Pat. Nos. 3,073,878; 3,080,438; 3,249,650; 3,515,770; 3,560,587; 3,686,354; 3,867,473 (Cl. 260-683.49); 3,925,502 (Cl. 260-683.48); 4,139,573 (Cl. 260-683.49) and 4,161,497 (Cl. 585-714). The process is also described in the article starting at page 78 of the Feb. 11, 1974 issue of *The Oil and Gas Journal*. These references describe process conditions, process equipment, the regeneration of the HF, and fractionation and treating procedures required in the process.

The isomerization of normal paraffins is described in U.S. Pat. Nos. 2,999,074; 3,112,351; 3,128,319; 3,283,021 (Cl. 260-666); 3,527,715 (Cl. 252-415); 3,649,704 (Cl. 260-668A); 3,652,697 (Cl. 260-668A); 3,798,082 (Cl. 260-683.68); and 3,506,733 (Cl. 260-683.68).

Processes for the dehydrogenation of paraffins are described in U.S. Pat. Nos. 3,391,218 (Cl. 260-683.3); 3,448,165 (Cl. 260683.3); 3,647,719 (Cl. 252-466PT); 3,649,566 (Cl. 252-470); 3,647,911 (Cl. 260-683.3); 3,714,281 (Cl. 260-668D); 3,742,078 (Cl. 260-668D); and 3,755,481 (Cl. 260-668D). These references describe the catalyst and process conditions which may be employed in the dehydrogenation of butanes. The preferred dehydrogenation catalyst is described in U.S. Pat. No. 3,745,112 (Cl. 208-139).

A multi-step process in which normal butanes are isomerized and the resultant isobutane is consumed in an alkylation zone by reaction with olefinic hydrocarbons is described in U.S. Pat. No. 3,931,352 (Cl. 260-683.49).

A multi-step process in which normal butanes are isomerized and the resultant isobutane is consumed in an alkylation zone by reaction with olefinic hydrocarbons is described in U.S. Pat. No. 3,931,352 (Cl. 260-683.49). U.S. Pat. No. 3,409,540 also illustrates the sequential steps of butane isomerization and alkylation.

U.S. Pat. No. 3,904,384 (Cl. 44-56) describes a multi-step process in which gasoline blending components are produced from normal and isobutane. The process includes the steps of fractionation, normal butane isomerization, thermal dehydrogenation of the isobutane and etheration of the isobutylene with isopropanol which is also produced in the process.

BRIEF SUMMARY OF THE INVENTION

The invention provides a process for the conversion of saturate butanes into gasoline and therefore facilitates the transportation and utilization of large quantities of natural gas which are not needed at their point of production. A broad embodiment of the invention may be characterized as a hydrocarbon conversion process which comprises the steps of passing a feed stream which comprises a mixture of normal butane and isobutane into a deisobutanizer column; withdrawing a first process stream, which is rich in normal butane, from the deisobutanizer column and passing the first process stream into a butane isomerization zone operated at isomerization conditions and thereby effecting the production of a butane isomerization zone effluent stream which comprises isobutane and normal butane; passing the butane isomerization zone effluent stream into the deisobutanizer column; withdrawing a second process stream, which is rich in isobutane, from the deisobutanizer column and passing the second process stream into a butane dehydrogenation zone and thereby producing a butane dehydrogenation zone effluent stream which comprises isobutane, isobutylene, and minor quantities of normal butane and normal butenes; heating the butane dehydrogenation zone effluent stream by indirect heat exchange against a stripper bottoms stream, and then passing the butane dehydrogenation zone effluent stream into a stripping column and thereby producing an overhead steam comprising propane and which is removed from the process and also producing said stripper bottoms stream, which comprises isobutane and isobutylene; cooling the stripper bottoms stream by indirect heat exchange against the butane dehydrogenation zone effluent stream, and passing the stripper bottoms stream into an alkylation zone in which HF is utilized as a catalyst and thereby producing an alkylation zone effluent stream which comprises normal butane, isobutane and $C_8$ branched-chain hydrocarbons; passing the alkylation zone effluent stream into an isostripper column and thereby producing an isostripper overhead stream comprising HF, isobutane and propane, an isostripper sidecut stream rich in isobutane and a net isostripper bottoms stream comprising $C_8$ branched-chain hydrocarbons, and withdrawing the isostripper bottoms stream from the process as a product stream; passing a first portion of the isostripper sidecut stream into the deisobutanizer column, utilizing a second portion of the isostripper sidecut stream to reboil the deisobutanizer column and then passing the second portion of the isostripper sidecut stream into the alkylation zone; condensing the isostripper overhead stream and passing substantially all of the hydrocarbons originally present in the isostripper overhead stream into an HF stripping column operated at conditions effective to separate the material charged to the column into an HF stripping column overhead stream comprising HF and a net HF stripping column bottoms stream comprising propane and isobutane; and passing a first portion of the HF stripping column bottoms stream into the stripping column and passing a second portion of the HF stripping column bottoms stream into the alkylation zone.

DESCRIPTION OF THE DRAWING

The Drawing illustrates two embodiments of the invention. This is not intended to remove from the inventive concept those other embodiments set out herein or which result from the modification of those embodiments. A feed stream which comprises a mixture of isobutane and normal butane enters the process through line 1 and is passed into a deisobutanizer column 2. The deisobutanizer is designed and operated to separate the entering process streams into a net overhead stream carried by line 3 which is rich in isobutane and a second stream removed through line 32 which is rich in normal butane.

A bottoms stream is removed from the bottom of the column in line 28 and divided into two portions, with a first portion carried by line 29 being passed through a reboiler 30. The remaining second portion of the bottoms stream is removed through line 32 as a normal butane rich net bottoms stream. If an optional lower sidecut stream is removed from the isostripper 16 in line 19, then substantially all of the normal butane in this sidecut becomes a part of the normal butane rich stream removed from the deisobutanizer. This is represented by the junction of lines 19 and 32. In either situation, the material in line 33 is passed into the butane isomerization zone 34 wherein it is contacted with a butane isomerization catalyst maintained at conditions effective to convert at least a substantial portion of the entering normal butane into isobutane. The light ends which are produced during the isomerization of the normal butane are removed from this zone in line 35. The resulting net hydrocarbonaceous effluent stream of the butane isomerization zone is carried by line 4 and is passed into the deisobutanizer column 2 at an intermediate point above the feed point.

The net overhead stream of the deisobutanizer column 2 is passed into the butane dehydrogenation zone 6. The entering hydrocarbons carried by line 3, which comprise isobutane and to a much lesser extent normal butane, are contacted with a dehydrogenation catalyst at conditions which effect the dehydrogenation of a substantial portion of the entering butanes and the production of butylenes. The net hydrogen production resulting from the dehydrogenation reaction is removed from the dehydrogenation zone in a line not shown. The net hydrocarbonaceous effluent of the dehydrogenation zone is carried by line 7 and is first heated in a heat exchanger 8 and is then passed into a stripper column 9, which is also referred to herein as the depropanizer column. The stripper column 9 is operated under conditions which effect the removal of substantially all propane and lighter hydrocarbons from the column as a net light ends stream which is removed through line 10 as the net overhead product of the column. A portion of these light ends is derived from the recycle stream passed into the stripping column through line 11.

A net bottoms stream which comprises substantially all of the C₄ hydrocarbons which enter the stripper column 9 is removed in line 12 and passed through the heat exchanger 8 to effect a heating of the butane dehydrogenation zone effluent stream. The hydrocarbons flowing through line 12 are admixed with the recycle stream carried by line 27 and passed into the alkylation zone 14 through line 13. The alkylation zone is operated under conditions which promote the alkylation reaction between the entering olefins and the entering isobutane. It is preferred that liquid phase HF (hydrofluoric acid) is utilized as the alkylation catalyst within this zone. The net hydrocarbonaceous effluent of the alkylation zone is passed into a fractionation column 16 normally referred to as an isostripper column through line 15.

The isostripper 16 is designed and operated to separate the entering hydrocarbons into a first sidecut stream carried to line 17 which is rich in isobutane, an optional lower second sidecut stream carried by line 19 which is rich in normal butane and a net bottoms stream carried by line 20 which contains the C₅-plus hydrocarbons produced in the alkylation zone. A first portion of the upper sidecut stream is passed through an alumina treater not shown to remove fluoride compounds and is then passed into the deisobutanizer 2 through line 5. The remaining second portion of the upper sidecut stream is carried by line 31 and is passed through the reboiler 30 of the deisobutanizer 2. This supplies at least a portion of the heat required to reboil the deisobutanizer and cools this portion of the upper sidecut stream, which is then passed into the alkylation zone via lines 27 and 13. The optional lower sidecut stream is admixed with the net deisobutanizer bottoms and passed into the butane isomerization zone.

The overhead vapor stream of the isostripper is carried by line 18 and passed through a condenser not shown and into a settler 21. The overhead vapor stream of the isostripper comprises a mixture of light hydrocarbons such as isobutane and propane and vapor-phase HF. The condensation of this mixture therefore produces both a hydrocarbon phase and a liquid HF phase which are separated within the settler 21. The less dense hydrocarbon phase is drawn off from the settler and passed into a fractionation column 24 normally referred to as an HF stripper through line 36. The overhead vapor stream of the HF stripper is removed in line 23 and contains vapor-phase HF and some propane. This overhead vapor stream is passed through a condenser not shown and into the settler 21. The liquid phase HF which accumulates in the settler is returned to the alkylation zone 14 through line 22.

A net bottoms stream is removed from the HF stripper in line 25 and divided into a first portion carried by line 26 and a second portion which is passed into column 9 through line 11. The stream flowing through line 11 is judiciously regulated to carry a sufficient amount of propane to the column 9 to insure the rejection of propane as light ends from this column at a rate equal to the sum of its production rate in the alkylation zone 14 and the rate of its passage into the alkylation zone. The remainder of the bottom stream of the HF stripper is passed through lines 26 and 27 to increase the supply of isobutane in the alkylation zone. The portion of the upper sidecut stream of the isostripper 16 carried by line 31 is also passed into line 27 to recycle this isobutane.

DETAILED DESCRIPTION

Large amounts of light hydrocarbons which were previously flared at the well site are now being collected and processed. It is expected that in several geographical areas, this will lead to an imbalance between the supply and the demand for butanes. It is an objective of this invention to provide a process for upgrading butanes into a gasoline blending stock. Such a process can alleviate the local excess supply of butanes which is expected to arise in various European and Arabic locations. The subject process will also allow the excess butanes to be converted into normally liquid hydrocarbons which are easily transported in conventional liquid carrying transports.

The feed stream to the subject process contains a mixture of isobutane and normal butane. Since this feed stream is expected to be derived from natural gas, the concentration of normal butane is expected to be several times greater than the concentration of isobutane. It is preferred that over 95 mole percent of the feed stream is C₄ hydrocarbons. It is also preferred that the feed stream contains as little C₅-plus hydrocarbons as is practical. The presence of pentane in the feed stream will require a slight modification of the process as described below. Several mole percent of propane is acceptable. The feed stream is passed into a first fractionation zone, which preferably comprises a single trayed column. As used herein, the term "fractionation zone" is intended to refer to the process equipment in which a specified separation is performed and may include one or more fractionation columns as desired. The fractionation zones also comprise such auxiliary equipment as reboilers, overhead vapor condensers and overhead receivers as may be required.

The preferred single column which functions as the first fractionation zone is referred to herein as the deisobutanizer or deisobutanizer column following the customary practice of referring to a column by its overhead product. It is the function of the deisobutanizer column to separate the entering streams into a net overhead stream which is rich in isobutane and a second stream which is rich in normal butane. As used herein, the term "rich" is intended to indicate that a process stream contains at least 55 mole percent of the particular hydrocarbon which is specified. It is believed that in most cases, a column containing about 40 trays will be sufficient as the deisobutanizer when correctly designed and operated. A representative set of operating conditions includes an overhead vapor temperature of approximately 38° C. at a pressure of about 80 psig.

The normal butane rich stream may be the bottoms stream of the deisobutanizer. However, there are two instances in which the normal butane rich stream will be removed from the deisobutanizer as a sidecut stream and a smaller bottoms stream will also be removed from the deisobutanizer. The first of these two situations is present when the feed stream contains pentane which would accumulate in the bottom of the deisobutanizer. The second situation occurs when it is desired to remove a lower second sidecut from the isostripper of the second fractionation zone. This sidecut stream will contain pentane and $C_8$ hydrocarbons which necessitate the removal of a bottoms stream from the deisobutanizer. Any deisobutanizer bottoms stream is preferably admixed with the bottoms stream of the isostripper to form the product stream removed from the process.

A second fractionation zone is also employed in the subject process. The alkylation zone effluent stream is passed into this zone, which preferably contains two distillation columns. The first column, which receives the net hydrocarbonaceous alkylation zone effluent, functions in a manner similar to the column normally referred to as the isostripper in HF alkylation units which produce motor fuel alkylate. A representative set of operating conditions for the isostripper includes an overhead vapor temperature of about 60° C. and an overhead pressure of approximately 150 psig. The isostripper may contain about 65 actual trays. Preferably the alkylation zone effluent stream enters the isostripper column at an upper intermediate point. A net overhead vapor stream, a net bottoms stream, and at least one sidecut stream are removed from the isostripper. The upper sidecut stream carries a large amount of the isobutane which has passed through the alkylation zone. A first portion of this isobutane-rich stream is recycled into the alkylation zone, with a second portion of this stream being passed into the deisobutanizer after being alumina-treated for the removal of fluoride compounds. If there is an excess of normal butane in the alkylation zone effluent stream, an optional lower sidecut stream is also withdrawn from the isostripper and passed into the deisobutanizer.

Any propane which is present in the feed stream to the alkylation zone or which are produced in the alkylation zone will enter the isostripper as part of the alkylation zone effluent stream. The propane is concentrated into the net overhead vapor of the isostripper. The overhead of the isostripper will also contain HF and some isobutane. Preferably, this overhead stream is passed through a condenser and the resultant condensate is separated into liquid hydrocarbon and liquid-phase HF streams in an overhead receiver which functions as a phase separation vessel. The liquid phase HF is recycled to the alkylation zone and the hydrocarbon phase is passed into a second fractionation column referred to as an HF stripper preferably at the top of this column. All of the HF dissolved in the hydrocarbon phase is concentrated into the overhead stream of the HF stripper, with this overhead stream being passed into the same condenser as the overhead of the isostripper. The HF is thereby separated and returned to the alkylation unit.

The bottoms stream of the HF stripper contains propane and some isobutane. The bottoms stream of the HF stripper is preferably divided into two portions, with a first portion being returned to the alkylation zone to recycle the isobutane and with a second portion being passed into a light ends stripping column located in the butane dehydrogenation zone. This column is used in the dehydrogenation zone to reject hydrogen and light ends. The recycling of some HF stripper bottoms liquid to this column thereby provides a means to remove from the process the propane present in the alkylation zone effluent stream without utilizing a separate depropanizer as is usually associated with HF alkylation units used for the production of motor fuel. However, this internal recycling of the HF stripper bottoms product to the dehydrogenation zone is not a requirement of the subject process, and a depropanizer column may be located within the second fractionation zone. Therefore in this alternative and unpreferred embodiment of the invention, the second fractionation zone will have three fractionation columns and a small stream of propane, not shown on the Drawing, will be removed from this zone.

The alkylate present in the net alkylation zone effluent stream is concentrated into a net isostripper bottoms stream. As previously described, in some embodiments of the process, this bottoms stream may be admixed with a small bottoms stream of the deisobutanizer column, which contains some normal butane and any $C_5$-plus hydrocarbons which enter the deisobutanizer column. This allows the rejection of any $C_5$-plus hydrocarbons which enter the deisobutanizer from the process and also facilitates the addition of normal butane to the final product. Some normal butane is normally required to be present in the alkylate to increase its vapor pressure up to that specified for gasoline. However, if the net alkylate product is intended for lengthy storage or transportation, it may be advisable to minimize the butane content of the product and to thereby lessen vaporization losses. The butane can then be blended into the alkylate at a later time.

The normal butane rich stream removed from the deisobutanizer is passed into a butane isomerization zone. This zone comprises a reactor and auxiliary process equipment such as heaters, condensers, separatory vessels, etc. The isomerization zone also contains a stripping column which eliminates hydrogen and light ends (methane and ethane) from the net effluent of the isomerization zone. With the preferred catalyst, this stripping column will also remove volatile chloride compounds from the isomerization zone effluent. The core of the operation of this zone is passage of the sidecut stream through a reactor maintained at butane isomerization-promoting conditions including the presence of an acidic isomerization catalyst. This is normally a relatively low pressure operation performed at a pressure of from about 50 to 600 psig. and at an elevated temperature as required by the activity of the catalyst. The average reactant temperature may be as high as 500° C., but is preferably between 100° C. and 320° C. It is normal practice to pass the butane through the reactor in admixture with between 1 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired. The effluent of the isomerization reactor is normally separated into a hydrogen-rich recycle gas which is returned to the reactor and an isomerate-containing liquid stream. It is within the scope of the inventive concept that this liquid stream may be fractionated to allow the recycling of normal butanes and the achievement of higher conversion rates, but this is not preferred. Further details on the butane isomerization step of the subject process may be obtained by referring to the previously cited references.

The preferred isomerization promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared substantially anhydrous gamma-alumina with a high degree of purity.

The preferred platinum group component is platinum, palladium or a mixture of platinum and palladium. This however is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt.% of the platinum group component, with the preferred concentration being from about 0.05 to about 1.0 wt.%. The method by which the platinum group component is made part of the catalytic composite is not controlling. It may therefore be added by co-precipitation or cogellation with the preferred carrier material or by ion-exchange or impregnation on pre-existing carrier material. The preferred method of preparing the catalyst impregnates the carrier material by contacting it with an aqueous solution of a water-soluble, decomposable compound of a platinum group metal. This may be performed by dipping the carrier material in a solution of chloroplatinic acid, ammonium chloroplatinate, bromoplatinic acid, or platinum dichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Alternatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt.% based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° C. to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

Recently developed isomerization catalysts are of a bimetallic or trimetallic nature. An example of this is the catalytic composite comprising a platinum group component, a germanium component, and a Friedel-Crafts metal halide component shown in U.S. Pat. No. 3,649,704. In U.S. Pat. No. 3,652,697, there is disclosed a trimetallic catalyst comprising a platinum group component, a germanium component, a rhenium component and a Friedel-Crafts metal halide component.

The net hydrocarbon effluent of the isomerization zone is a mixture of isobutane and normal butane. This stream and a portion of the isobutane-rich recycle stream produced in the second fractionation zone are both passed into the deisobutanizer. Substantially all of the isobutane which enters the deisobutanizer is concentrated into a net overhead stream and passed into the butane dehydrogenation zone wherein isobutane is converted into isobutylene. This zone will contain a reaction zone and associated auxiliary process equipment. The auxiliary equipment should include coolers, condensers and a vapor-liquid separator designed to produce hydrogen-rich recycle and net gas streams. This separator may be operated at a pressure of 200 psig. and temperature of −40° C. The separation facilities of the dehydrogenation zone also includes at least one fractionation column. This column is designed and operated to eliminate all ethane and lighter boiling components from the net dehydrogenation zone effluent stream. It may also separate some and possibly all of the propylene into the light ends stream removed from this zone. When a propane-containing recycle stream is passes into the fractionation column from the second fractionation zone the column is designed and operated to remove propane as part of its net overhead stream, which becomes the light ends stream of the dehydrogenation zone. The removal of ethane is necessary since the carry-over of this light material into an HF alkylation zone will cause a loss of HF in net overhead vapors in the second fractionation zone. If a different alkylation catalyst is used, the presence of ethane in the alkylation zone feed stream may be acceptable. Propylene may be present at this point in the process due to the dehydrogenation of propane found in the feed stream to the process or from the cracking of butanes and the production of the light ends removed from this zone.

The reaction zone of the butane dehydrogenation zone preferably comprises at least one radial flow reactor in which the catalyst gradually moves downward by gravity flow to allow the continuous replacement of used catalyst with catalyst having a higher activity. It is preferred that a multistage moving bed reactor is employed. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887 and 3,856,662.

The particular dehydrogenation conditions employed within the dehydrogenation zone may vary depending on such factors as the catalyst activity, feed carbon number and the desired conversion. The conditions normally employed for isobutane dehydrogenation include a temperature of from about 500° C. to 700° C., a pressure of from 0.5 to about 10 atmospheres of pressure and a liquid hourly space velocity of about 1 to 20 hr.$^{-1}$. The preferred operating temperature will be within the range of from about 550° C. to 650° C., and the preferred operating pressure is about 0.5 to 2 atmospheres.

The preferred butane dehydrogenation catalyst is comprised of a platinum group component, a tin component and an alkali metal component with a porous inorganic carrier material. Other catalytic compositions may be used within this zone if desired.

It is preferred that the porous carrier material is an absorptive high surface area support having a surface area of about 25 to about 500 m$^2$/g. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide with the best results being obtained with an alumina carrier material. The crystalline aluminas, such as gamma alumina, give the best results. In general, the preferred catalysts will have a gamma alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide to a salt of alumina such as aluminum chloride in an amount to form an aluminum hydroxide gel which upon drying and calcining, is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° C. to about 200° C. and calcined at a temperature of about 450° C. to about 700° C. for a period of about 1 to about 20 hours. See the teachings of U.S. Pat. No. 2,620,314 for additional details on the preparation of the base material by the oil dropping method.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt.% of the final catalytic composite, calculated on an elemental basis. It is preferred that the platinum content of the catalyst is between about 0.1 and 1.0 wt.%. The preferred platinum group component is platinum, with palladium being the next preferred metal. The platinum group component may be incorporated into the catalytic composite in any suitable manner such as by coprecipitation or cogellation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred catalyst should constitute about 0.01 to about 5 wt.% of the final composite, calculated on an elemental basis, although substantially higher amounts of tin may be utilized in some cases. Best results are often obtained with about 0.1 to about 1 wt.% tin. It is preferred that the atomic ratio of tin to platinum is between 1:1 to about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitating it during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred butane dehydrogenation catalyst contains less than 0.5 wt.% halogen and preferably less than 0.1 wt.% halogen. Residual amounts of any halogen, such as chlorine, at or below this concentration may be tolerated. The preferred catalyst does however contain an alkali metal component chosen from cesium, rubidium, potassium, sodium, and lithium. The preferred alkali metal is lithium. The concentration of the alkali metal may range from between 0.1 and 3.5 wt.% but is preferably between 0.2 and about 1.5 wt.% calculated on an elemental basis.

The net $C_3$-plus effluent of the dehydrogenation zone is passed into an alkylation zone. An isobutane-rich recycle stream removed from the isostripper of the second fractionation zone is also passed into the alkylation zone. These two streams may be admixed prior to their passage into the alkylation zone. The dehydrogenation zone effluent stream may contain some propylene formed by the dehydrogenation of propane present in the feed stream. This propylene is consumed in the same manner as the butylenes by reaction with the isobutane. The term "alkylation zone" is intended to indicate a sequence of processing equipment in which the entering reactants are contacted with an alkylation catalyst maintained at alkylation-promoting conditions including one or more reaction zones and the required equipment for the separation and recovery of the resultant alkylate from process streams within the alkylation zone. It is preferred that the alkylation zone contains no fractionation columns other than that used for catalyst regeneration.

The alkylation reaction is promoted by the presence of a mineral acid catalyst such as hydrofluoric acid, sulfuric acid or phosphoric acid. These acids are maintained in a liquid phase containing a minimum of water to reduce corrosion problems. The maximum amount of water normally allowed in the acid is about 5 wt.%. When fresh acid is charged to a plant, it is normally very dry and contains about 0.5 percent water or less. The catalyst may also comprise a mixture of a mineral acid and a Friedel-Crafts metal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 psig. to about 500 psig., and a more preferred range being from 100 psig. to about 250 psig. It is preferred that the pressure within the reactant-catalyst contacting vessel is approximately 150 psig. and essentially "floats" on the pressure maintained in the downstream second fractionation zone. Although the alkylation reaction may be performed at temperatures from below $-18°$ C. to about 90° C., it is preferred to operate the commercially prevalent isoparaffin-olefin alkylation process in the range of from about 10° C. to about 60° C., with 32° C. being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. If there is a shortage of isobutane in the alkylation zone, a portion of the deisobutanizer overhead stream may be passed directly into the alkylation zone. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They would however have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of venturies or mixing nozzles are normally utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into the isostripper. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the previously cited references.

The net hydrocarbonaceous effluent stream of the alkylation zone is passed into the isostripper of the second fractionation zone. This isostripper is similar to that normally associated with HF catalyst motor fuel alkylation units. The isostripper recovers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in the alkylation zone in this instance. The sidecut stream rich in isobutane and the optional sidecut stream rich in normal butane are removed from the isostripper for recycling. If HF is utilized as the catalyst in the alkylation zone, fluoride compounds will normally be present in these recycle streams. These streams should then be passed through a fluoride removal zone comprising an alumina treater and a caustic contacting zone when the fluoride compounds will be detrimental to any catalyst which they may contact. This is often the case with chloride promoted isomerization catalysts. Such treatment is required with the preferred isomerization catalyst. Any portion of either recycle stream which is passed into the deisobutanizer should be treated.

One embodiment of the invention may be characterized as a hydrocarbon conversion process which comprises the steps of passing a feed stream which comprises a mixture of normal butane and isobutane into a deisobutanizer column operated at effective fractionation conditions; withdrawing a first process stream, which is rich in normal butane, from the deisobutanizer column and passing the first process stream into a butane isomerization zone operated at isomerization conditions and thereby effecting the production of a butane isomerization zone effluent stream which comprises isobutane and normal butane; passing the butane isomerization zone effluent stream into the deisobutanizer column; withdrawing a second process stream, which is rich in isobutane, from the deisobutanizer column and passing the second process stream into a butane dehydrogenation zone operated at butane dehydrogenation conditions and thereby effecting the formation of a butane dehydrogenation zone effluent stream which comprises isobutane, isobutylene, normal butane and normal butenes; heating the butane dehydrogenation zone effluent stream by indirect heat exchange against a stripper bottoms streams, and then passing the butane dehydrogenation zone effluent stream into a stripping column operated at effective fractionation conditions and thereby producing an overhead stream comprising propane and which is removed from the process and said stripper bottoms stream which comprises isobutane, isobutylene and normal butane; cooling the stripper bottoms stream by indirect heat exchange against the butane dehydrogenation zone effluent stream, and passing the stripper bottoms stream into an alkylation zone operated at alkylation-promoting conditions and in which HF is utilized as a catalyst and thereby producing an alkylation zone effluent stream which comprises normal butane, isobutane and $C_8$ branched-chain hydrocarbons; passing the alkylation zone effluent stream into an isostripper column operated at effective fractionation conditions and thereby producing an isostripper overhead stream comprising HF, isobutane and propane, a first isostripper sidecut stream, which is rich in isobutane, a second isostripper sidecut stream, which is rich in normal butane, and a net isostripper bottoms stream comprising $C_8$ branched-chain hydrocarbons, and withdrawing the isostripper bottoms stream from the process as a product stream; passing a first portion of the first isostripper sidecut stream into the deisobutanizer column, utilizing a second portion of the first isostripper sidecut stream to reboil the deisobutanizer column and then passing the second portion of the first isostripper sidecut stream into the alkylation zone; passing the second isostripper sidecut stream into the deisobutanizer column; condensing the isostripper overhead stream and passing substantially all of the hydrocarbons originally present in the isostripper overhead stream into an HF stripping column operated at conditions effective to separate the material charged to the column into an HF stripping column overhead stream comprising HF and a net HF stripping column bottoms stream comprising propane and isobutane; and, passing a first portion of the HF stripping column bottoms stream into the stripping column and passing a second portion of the HF stripping column bottoms stream into the alkylation zone.

The removal of a normal butane rich lower sidecut stream from the isostripper column is an optional step in the overall process. The basic determinant of when this sidecut stream is withdrawn is the amount of normal butane which enters the isostripper. A lower sidecut stream is taken only if the rate at which normal butane enters the isostripper exceeds the total of the maximum acceptable rates at which the normal butane can be withdrawn in the upper sidecut stream and the bottoms stream. The rate at which normal butane enters the isostripper is dependent on the separatory capability and operation of the deisobutanizer and conversion rate achieved in the butane dehydrogenation zone. The lower sidecut stream will contain some heavier $C_8$ hydrocarbons produced in the alkylation zone. The sidecut stream is therefore passed directly into the deisobutanizer to concentrate these heavier compounds in the deisobutanizer bottoms stream. The normal butane rich stream which is fed to the isomerization zone is therefore removed from the deisobutanizer as a sidecut stream.

In the subject process, the required heat exchange steps are integrated to reduce the overall utilities cost of operating the process. Heat is recovered from the bottoms stream of the dehydrogenation zone stripping column by the indirect heat exchange against the dehydrogenation zone effluent stream. Heat is also recovered from the upper sidecut stream of the isostripper by utilizing at least a portion of this stream to at least partially reboil the deisobutanizer column. This may be done in two ways. In the embodiment shown in the Drawing, the upper sidecut stream is divided into two portions, with only one portion being heat exchanged against the bottoms liquid of the deisobutanizer. The other portion is passed through an alumina treater (not shown) to remove fluoride compounds and is then passed into the deisobutanizer. In a more complex embodiment of the process, the effluent of the alumina treater, which will normally be at a temperature of about 400° F., is also used to reboil the deisobutanizer. Preferably, the bottoms liquid of the deisobutanizer would be heat exchanged first against the undefluorinated portion of the sidecut stream and then against the effluent of the alumina treater. This heat exchange may supply a part or all of the heat required to reboil the deisobutanizer. In either case, the effluent of the alumina treater is eventually cooled, normally with the assistance of external coolers, to a temperature close to 120° F. and is then passed into the top portion of the deisobutanizer column. Depending on such factors as the composition of the hydrocarbons charged to the deisobutanizer, this stream may be used to provide some or all of the reflux to the deisobutanizer.

It is contemplated that heat may also be recovered from other relatively hot process streams in the process such as the net bottoms streams of the deisobutanizer and the isostripper by the indirect heat exchange of these streams against the feed streams to these columns or other streams which require heating. The required heat exchange may be performed in any of the customary types of apparatus which are now in widespread commercial usage. However, it is preferred that shell and tube type heat exchangers are employed in the process.

In order to ensure a complete understanding of the subject process, a projected rough material balance of a processing unit having an overall flow similar to that shown in the Drawing is given below. The optional lower sidecut stream of line 19 is not utilized. The line numbers designated in the Table correspond to lines on the Drawing. The relatively small light ends and hydrogen flows are not given. The material balance is for a unit in which all propylene produced in the butane dehydrogenation zone is removed from the process as part of the stripping column overhead stream. All quantities are given in metric tons per stream day. The normal butane rich stream is removed from the deisobutanizer as a sidecut stream and a bottoms drag stream having a flow rate of 43.1 metric is removed from the deisobutanizer and blended with the isostripper bottoms stream.

| Line | 1 | 3 | 4 | 5 | 11 | 12 | 20 | 33 |
|---|---|---|---|---|---|---|---|---|
| Propane | 6.7 | 25.6 | — | 18.9 | 5.8 | 24.6 | — | — |
| Isobutylene | — | — | — | — | — | 457.7 | — | — |
| Isobutane | 265.9 | 1681.8 | 810.9 | 665.6 | 43.1 | 1209.3 | 1.1 | 60.6 |
| n-Butene | — | — | — | — | — | 11.7 | — | — |
| n-Butane | 838.4 | 78.9 | 690.5 | 41.2 | 2.9 | 67.6 | 32.3 | 1455.9 |
| Isopentane | — | — | 55.3 | 3.7 | — | — | 20.3 | 55.3 |
| $C_6$-Plus | — | — | — | 4.2 | — | — | 930.9 | — |

I claim as my invention:

1. A hydrocarbon conversion process which comprises the steps of:
  (a) passing a feed stream which comprises a mixture of normal butane and isobutane into a deisobutanizer column operated at effective fractionation conditions;
  (b) withdrawing a first process stream, which is rich in normal butane, from the deisobutanizer column and passing the first process stream into a butane isomerization zone operated at isomerization conditions and thereby effecting the production of a butane isomerization zone effluent stream which comprises isobutane and normal butane;
  (c) passing the butane isomerization zone effluent stream into the deisobutanizer column;
  (d) withdrawing a second process stream, which is rich in isobutane, from the deisobutanizer column and passing the second process stream into a butane dehydrogenation zone operated at butane dehydrogenation conditions and thereby effecting the formation of a butane dehydrogenation zone effluent stream which comprises isobutane, isobutylene, normal butane and normal butenes;
  (e) heating the butane dehydrogenation zone effluent stream by indirect heat exchange against a stripper bottoms stream, and then passing the butane dehydrogenation zone effluent stream into a stripping column operated at effective fractionation conditions and thereby producing an overhead stream comprising propane and which is removed from the process and said stripper bottoms stream which comprises isobutane, isobutylene, normal butane and normal butenes;
  (f) cooling the stripper bottoms stream by indirect heat exchange against the butane dehydrogenation zone effluent stream, and passing the stripper bottoms stream into an alkylation zone operated at alkylation-promoting conditions and in which HF is utilized as a catalyst and thereby producing an alkylation zone effluent stream which comprises normal butane, isobutane and $C_8$ branched-chain hydrocarbons;
  (g) passing the alkylation zone effluent stream into an isostripper column operated at effective fractionation conditions and thereby producing an isostripper overhead stream comprising HF, isobutane and propane, an isostripper sidecut stream rich in isobutane and a net isostripper bottoms stream comprising $C_8$ branched-chain hydrocarbons, and withdrawing the isostripper bottoms stream from the process as a product stream;
  (h) passing a first portion of the isostripper sidecut stream into the deisobutanizer column, utilizing a second portion of the isostripper sidecut stream to reboil the deisobutanizer column and then passing the second portion of the isostripper sidecut stream into the alkylation zone;
  (i) condensing the isostripper overhead stream and passing substantially all of the hydrocarbons originally present in the isostripper overhead stream into an HF stripping column operated at conditions effective to separate the material charged to the column into an HF stripping column overhead stream comprising HF and a net HF stripping column bottoms stream comprising propane and isobutane; and,
  (j) passing a first portion of the HF stripping column bottoms stream into the stripping column of step (e) and passing a second portion of the HF stripping column bottoms stream into the alkylation zone.

2. The process of claim 1 further characterized in that a second isostripper sidecut stream, which is rich in normal butane, is removed from the isostripper column and passed into the deisobutanizer column.

3. The process of claim 1 further characterized in that the butane dehydrogenation zone contains a catalytic composite comprising platinum, tin and lithium.

4. The process of claim 3 further characterized in that the butane isomerization zone contains a catalytic composite comprising a platinum group metal and a Friedel-Crafts metal halide.

5. A hydrocarbon conversion process which comprises the steps of:
   (a) passing a feed stream which comprises a mixture of normal butane and isobutane into a deisobutanizer column operated at effective fractionation conditions;
   (b) withdrawing a first process stream, which is rich in normal butane, from the deisobutanizer column and passing the first process stream into a butane isomerization zone operated at isomerization conditions and thereby effecting the production of a butane isomerization zone effluent stream which comprises isobutane and normal butane;
   (c) passing the butane isomerization zone effluent stream into the deisobutanizer column;
   (d) withdrawing a second process stream, which is rich in isobutane, from the deisobutanizer column and passing the second process stream into a butane dehydrogenation zone operated at butane dehydrogenation conditions and thereby effecting the formation of a butane dehydrogenation zone effluent stream which comprises isobutane, isobutylene, normal butane and normal butenes;
   (e) heating the butane dehydrogenation zone effluent stream by indirect heat exchange against a stripper bottoms stream, and then passing the butane dehydrogenation zone effluent stream into a stripping column operated at effective fractionation conditions and thereby producing an overhead stream comprising propane and which is removed from the process and said stripper bottoms stream which comprises normal butane, isobutane and isobutylene;
   (f) cooling the stripper bottoms stream by indirect heat exchange against the butane dehydrogenation zone effluent stream, and passing the stripper bottoms stream into an alkylation zone operated at alkylation-promoting conditions and in which HF is utilized as a catalyst and thereby producing an alkylation zone effluent stream which comprises normal butane, isobutane and $C_8$ branched-chain hydrocarbons;
   (g) passing the alkylation zone effluent stream into an isostripper column operated at effective fractionation conditions and thereby producing an isostripper overhead stream comprising HF, isobutane and propane, an isostripper sidecut stream rich in isobutane and a net isostripper bottoms stream comprising $C_8$ branched-chain hydrocarbons, and withdrawing the isostripper bottoms stream from the process as a product stream;
   (h) heat exchanging a first portion of the isostripper sidecut stream against the bottoms liquid of the deisobutanizer column to at least partially reboil the deisobutanizer column and then passing the first portion of the isostripper sidecut stream into the alkylation zone, passing a second portion of the isostripper sidecut stream through an alumina treater to remove fluoride compounds, utilizing the second portion of the isostripper sidecut stream to at least partially reboil the deisobutanizer column and then passing the second portion of the isostripper sidecut stream into the deisobutanizer column;
   (i) condensing the isostripper overhead stream and passing substantially all of the hydrocarbons originally present in the isostripper overhead stream into an HF stripping column operated at conditions effective to separate the material charged to the column into an HF stripping column overhead stream comprising HF and a net HF stripping column bottoms stream comprising propane and isobutane; and,
   (j) passing a first portion of the HF stripping column bottoms stream into the stripping column of step (e) and passing a second portion of the HF stripping column bottoms stream into the alkylation zone.

6. The process of claim 5 further characterized in that a second isostripper sidecut stream, which is rich in normal butane, is removed from the isostripper column and passed into the deisobutanizer column.

7. The process of claim 5 further characterized in that the butane dehydrogenation zone contains a catalytic composite comprising platinum, tin and lithium.

8. The process of claim 7 further characterized in that the butane isomerization zone contains a catalytic composite comprising a platinum group metal and a Friedel-Crafts metal halide.

* * * * *